United States Patent
Togashi (10) Patent No.: US 8,790,312 B2
(45) Date of Patent: Jul. 29, 2014

(54) NEEDLE-EQUIPPED SYRINGE BARREL AND NEEDLE-EQUIPPED SYRINGE

(75) Inventor: Hiroshi Togashi, Tokyo (JP)

(73) Assignee: Daikyo Seiko Ltd., Tokyo (JP)

( * ) Notice: Subject to any disclaimer, the term of this patent is extended or adjusted under 35 U.S.C. 154(b) by 1136 days.

(21) Appl. No.: 12/451,008

(22) PCT Filed: Apr. 25, 2008

(86) PCT No.: PCT/JP2008/058447
§ 371 (c)(1),
(2), (4) Date: Dec. 23, 2009

(87) PCT Pub. No.: WO2008/139982
PCT Pub. Date: Nov. 20, 2008

(65) Prior Publication Data
US 2010/0145284 A1 Jun. 10, 2010

(30) Foreign Application Priority Data
Apr. 26, 2007 (JP) .................. 2007-117765

(51) Int. Cl.
*A61M 5/00* (2006.01)
*B29C 45/14* (2006.01)
*A61M 5/34* (2006.01)
*A61M 5/31* (2006.01)
*B29L 31/00* (2006.01)

(52) U.S. Cl.
CPC .......... *A61M 5/346* (2013.01); *B29C 45/14065* (2013.01); *A61M 5/3134* (2013.01); *B29L 2031/7544* (2013.01); *B29C 45/14426* (2013.01); *A61M 5/34* (2013.01)
USPC ............................................ 604/187; 604/218

(58) Field of Classification Search
USPC .................. 604/181, 187, 192–198, 218–231
See application file for complete search history.

(56) References Cited

U.S. PATENT DOCUMENTS

| 3,118,448 A | 1/1964 | Gottschalk |
| 3,330,004 A | 7/1967 | Cloyd et al. |

(Continued)

FOREIGN PATENT DOCUMENTS

| FR | 891 892 A | 3/1944 |
| JP | S47-7896 A | 4/1972 |

(Continued)

OTHER PUBLICATIONS

European Patent Office, "Extended European Search Report for RP 08 76 4255", Oct. 10, 2013.

(Continued)

*Primary Examiner* — Kevin C Sirmons
*Assistant Examiner* — Phillip Gray
(74) *Attorney, Agent, or Firm* — Manabu Kanesaka (57) ABSTRACT

There are provided a needle-equipped syringe barrel and a needle-equipped syringe in which a needle is suitably fixed to a syringe nozzle, and a mold and a method for molding thereof. A metal needle 12 is integrally equipped to a synthetic resin syringe nozzle 113 by integral molding, an area where the needle 12 comes into contact with the nozzle 113 being in a range of 11 to 50 mm². A needle-equipped syringe barrel 1 in which a metal needle 12 is integrally equipped to a synthetic resin syringe nozzle 113 by integral molding, height of a needle end 122 extruded toward an inner hollow portion thereof opposite to a needle head 121 being in a range of 0.4 to 11 mm.

7 Claims, 9 Drawing Sheets

(56) References Cited

U.S. PATENT DOCUMENTS

| | | |
|---|---|---|
| 3,402,713 A | 9/1968 | Senkowski et al. |
| 4,354,495 A | 10/1982 | Bodicky |
| 4,956,143 A | 9/1990 | McFarlane |
| 5,085,640 A * | 2/1992 | Gibbs .......................... 604/110 |
| 5,693,026 A | 12/1997 | Spinello |
| 6,344,034 B1 * | 2/2002 | Sudo et al. .................... 604/263 |
| 2002/0138042 A1 | 9/2002 | Llorach et al. |
| 2004/0078008 A1 | 4/2004 | Ueda et al. |
| 2006/0079848 A1 | 4/2006 | Pelkey et al. |
| 2010/0145284 A1 | 6/2010 | Togashi |

FOREIGN PATENT DOCUMENTS

| | | |
|---|---|---|
| JP | S50-002557 | 1/1975 |
| JP | H07-047045 | 5/1995 |
| JP | H09-066104 | 3/1997 |
| JP | 2006-116217 | 5/2006 |
| WO | 2008/139982 A1 | 11/2008 |

OTHER PUBLICATIONS

Japan Patent Office, "Office Action for JP 2009-514125," Jan. 24, 2014.

Japan Patent Office, "Submission of Information for JP 2009-538288", Jan. 24, 2013.

Japanese Standards Association, "Sterile Injection Needles", JIS T3209, Corresponding International Standards ISO 7864.

Japanese Standards Association, "Sterile single-use syringes, with or without needle, for insulin", JIS T3253, Corresponding International Standards ISO 8537.

* cited by examiner

Fig. 1(A)

Elevation
(in the direction F1)

Fig. 1(B)

Rear Elevation
(in the direction F2)

NEEDLE-EQUIPPED SYRINGE BARREL AND NEEDLE-EQUIPPED SYRINGE

FIELD OF THE INVENTION

This invention relates to a needle-equipped syringe barrel and a needle-equipped syringe in which a needle is suitably fixed to a syringe nozzle, and a mold and method for molding thereof.

BACKGROUND TECHNOLOGY

Heretofore, there have been known syringes in which a needle is integrally fixed to a glass syringe barrel as a needle-equipped syringe. The needle should be securely fixed to a syringe nozzle in such needle-equipped syringes, however, it is not easy to keep a tightly closed condition between the needle and the glass syringe nozzle to be fixed thereto because of inferior compatibility between metal and glass.

Further, as dimensional accuracy of conventional needle-equipped glass syringe barrels is generally low, it is difficult to mass produce them stably. In a conventional method of glass syringe barrel production, a thin metal bar such as tungsten is temporarily set at a nozzle head to form a hole for needle during glass molding, which is removed to fix a needle after the syringe barrel is molded.

According to this method, however, metal (tungsten) might remain and stick in the syringe barrel and is to be washed off by an additional after treatment, or else an interaction of the metal with injection liquid would arose a problem of aggregation caused by an insoluble substance.

Figure 8:
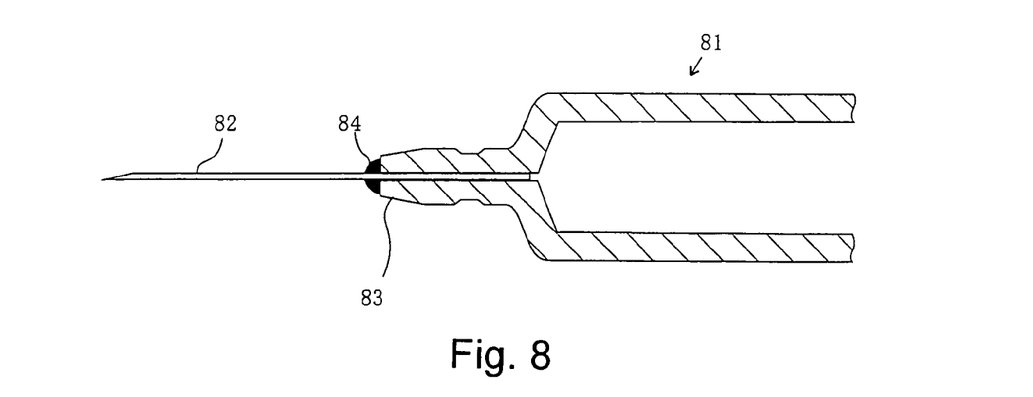
FIG. 8 is a sectional illustration of a conventionally injection molded syringe barrel in which a needle is fixed by means of an adhesive.

In order to avoid disadvantages as described above, a resin syringe barrel has also been produced by injection molding as shown, for example, in FIG. 8. According to such a conventional method, it is an essential process to fix a needle 82 to a nozzle 83 by means of an adhesive 84 to complete a syringe barrel 81, thereby inconveniently lowering the productivity. A ingredient of the adhesive might cause a problem of injection contamination.

There has been proposed another type of needle-equipped resin syringe barrel produced by injection molding for the purpose of resolving above mentioned inconvenience (see, for example, Japanese Patent A No. 9-66104 as a cited patent literature No. 1). In this case, the process of injection molding itself is advantageous to mass production, however, fixing strength of the needle to the syringe barrel should necessarily be guaranteed.

As is unclear from the patent literature No. 1, no novel technique has been known on a connecting structure of the needle and the syringe nozzle or a structure of mold, for example, a setting manner of the needle in the mold. That is to say, a technique to integrate the needle and the resin syringe barrel is quite poor at present.

Injection molding of needle-equipped syringe barrels using a synthetic resin is anticipated to be done in the following manner.

Figure 9A:
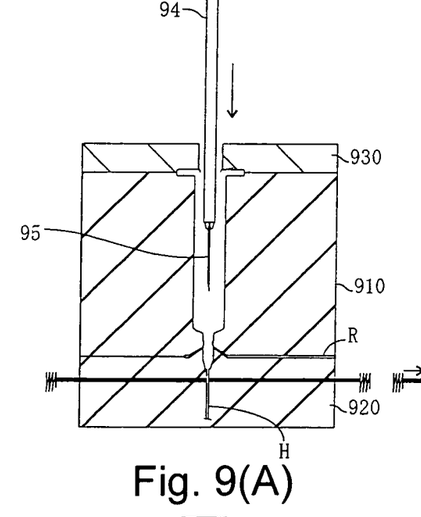
FIG. 9 is a sectional illustration of a mold used to conventionally mold a needle-equipped syringe barrel, in which (A) to (D) show a manner of molding.
Figure 9B:
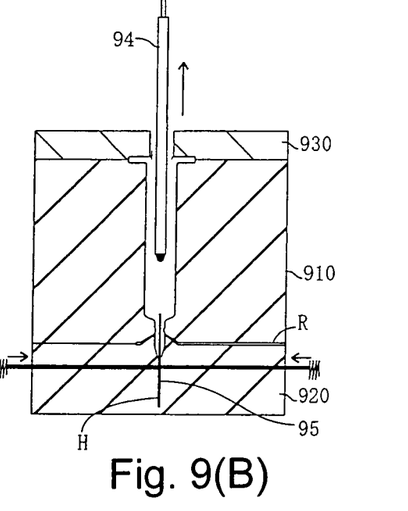

A core plate 930 is closed, followed by introduction of a needle carrying rod 94 provided with a needle 95 on a head thereof into a space formed by a cavity plate 910 as shown in FIG. 9(A). The needle 95 is then arranged in a needle holding hole H formed on a runner plate 920 and the carrying rod 94 is receded upward as shown in FIG. 9(B).

Figure 9C:
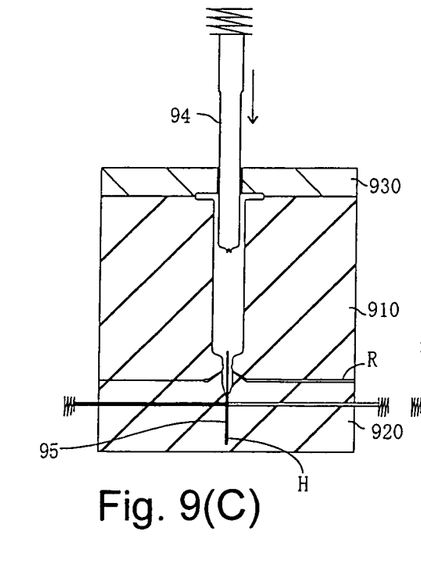

An inner mold 94 is inserted in the above mentioned space as shown in FIG. 9(C). In this situation, a cavity of a definite gap is formed between an outer surface of the inner mold 94 and a hollow wall surface of the cavity plate 910, which is not shown in the figure.

Figure 9D:
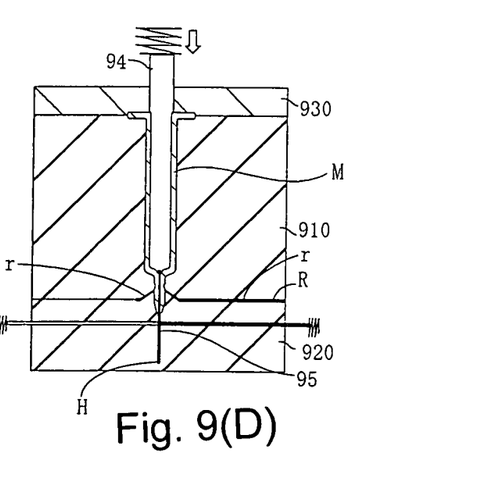
Figure 10:
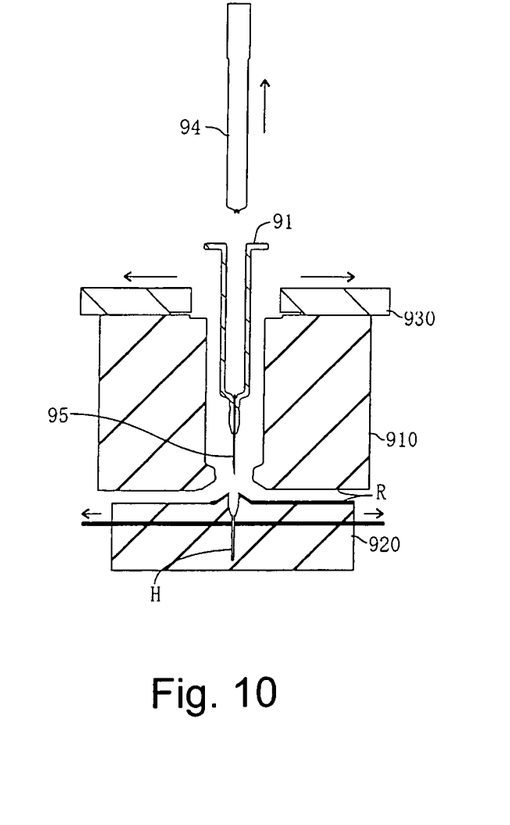
FIG. 10 is an illustration for showing a manner to take out the molded syringe barrel in the mold in FIG. 9.

A resin is injected into the cavity as shown in FIG. 9(D) in which symbols M and r designate thus injected resin and a runner molded part as a runner product molded by a runner R, respectively. Then, the cavity plate 910 and a core plate 930 are opened to take out a syringe barrel 91 as shown in FIG. 10, while the runner product r is also taken out.

DETAILED DESCRIPTION

Problems to be Solved by the Invention

Figure 11A:
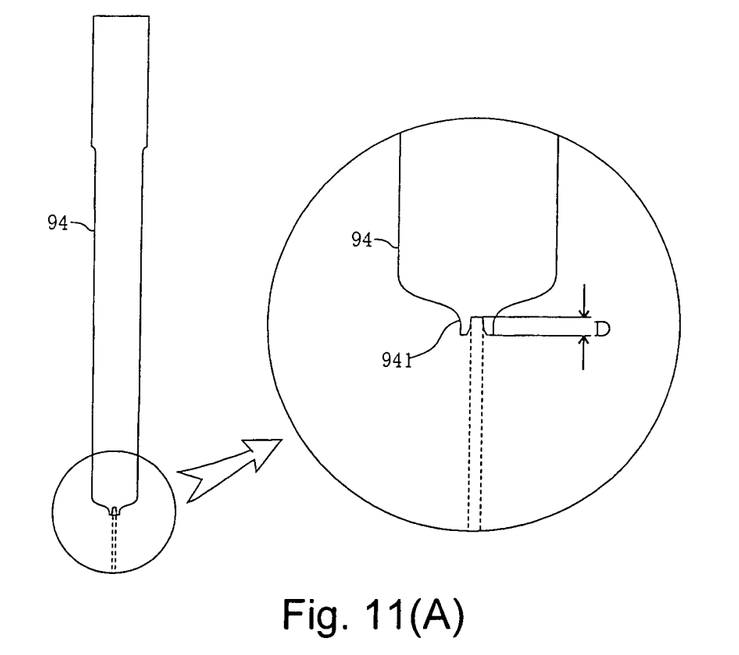
FIGS. 11(A), (B) show forms at a tip portion of an inner mold in order to prevent an injected material from permeating into a needle capillary.
Figure 11B:
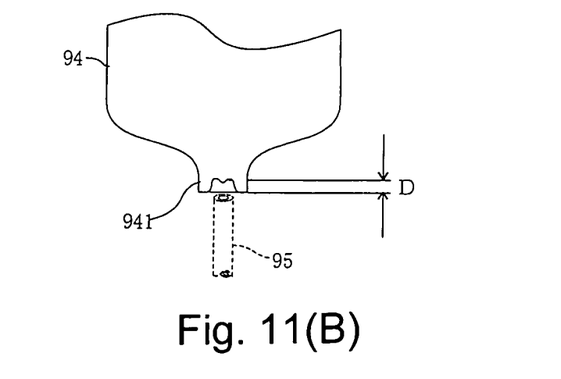

An end of the inner mold 94 should be a structure as shown in FIGS. 11(A) and (B) so as to prevent an injected material from permeating into a needle capillary. More precisely, it is necessary to form a concave portion at a tip portion of the inner mold 94 so as to plunge a needle rear end opposite to a needle head, and to control such permeation from the needle rear end. As a result, height D of the end portion extruded toward an inner hollow portion of the syringe barrel inevitably increases, thereby leaving a considerable amount of an injection liquid in a syringe after injection is done.

Further, a silicone resin or silicone oil is sometimes coated or deposited on the inside surface of the syringe barrel 91 to slide a piston more easily, but might arise various anxiety such as adsorption of effective ingredients in the injection liquid, formation of insoluble substances as a reaction product thereof with the injection liquid, i.e., aggregation, and bad influence upon human body caused by a mixture thereof with the liquid injected in the body.

Accordingly, it is an object of the invention to provide a needle-equipped syringe barrel and a needle-equipped syringe in which a needle is securely fixed to the syringe barrel while steadily keeping adhesivity or sealability around a fixing portion thereof to a syringe nozzle, and a mold as well as a method for preparing the needle-equipped syringe barrel.

Another object of the invention is to provide a needle-equipped syringe comprising said needle-equipped syringe barrel as a composing element without arising problems derived from a silicone resin component.

Yet another object of the invention is to provide a needle-equipped syringe barrel and a needle-equipped syringe in which an injected material is less permeable into a needle capillary when the syringe barrel is injection molded and height of a needle end opposite to a needle head extruded toward an inner hollow portion of the syringe barrel is decreased, a mold and method for molding said syringe barrel.

Means to Solve the Problems

A needle-equipped syringe barrel of the invention comprises the following items (1) to (3):

(1) A needle-equipped syringe barrel in which a metal needle of 25 to 34 G in thickness is integrally equipped to a synthetic resin syringe nozzle by integral molding, characterized in that an area where the needle comes into contact with the syringe nozzle falls in a range of 11 to 50 $mm^2$;

(2) A needle-equipped syringe barrel described in item (1) in which height of a needle rear end extruded toward an inner hollow portion thereof opposite to a needle head falls within a range of 0.4 to 11 mm; and (3) A needle-equipped syringe barrel in which a metal needle is integrally equipped to a synthetic resin syringe nozzle by integral molding, characterized in that height of a needle rear end extruded toward an inner hollow portion thereof opposite to a needle head falls in a range of 0.4 to 11 mm.

A needle-equipped syringe of the invention comprises the following item (4):

(4) A needle-equipped syringe barrel comprising a syringe barrel described in any item (1), (2) or (3), characterized in that the syringe barrel is not inner-treated and a piston thereof is laminated with a fluorine resin.

A mold for molding a needle-equipped syringe barrel comprises the following items (5) and (6):

(5) A mold for preparing a needle-equipped syringe barrel comprising an inner mold of a contour corresponding to an interior contour of the inner syringe barrel, in which a concave portion is formed at a tip portion thereof to hold a needle rear end opposite to a needle head, and an outer mold of a contour corresponding to exterior contours of an outer syringe barrel and of an outer syringe nozzle, characterized in that a needle is kept in a region corresponding to a needle head in the outer mold, a needle holder being fitted to elastically push up the needle rear end to the concave portion of the inner mold; and (6) A mold for molding a needle-equipped syringe barrel described in item (5) in which the needle rear end opposite to the needle head is pressed to the concave portion of the inner mold by pinning the needle head against an elastic material or spring through a needle head protector when the mold is closed.

A method for molding a needle-equipped syringe barrel of the invention comprises the following item (7):

(7) A method for molding a needle-equipped syringe barrel by arranging an inner mold of a contour corresponding to an interior contour of the inner syringe barrel, in which a concave portion is formed at a tip portion thereof to hold a needle rear end opposite to a needle head, in an outer mold of a contour corresponding to exterior contours of the outer syringe barrel and of an outer syringe nozzle, characterized in that a needle is kept in a region corresponding to a needle head and the needle rear end opposite to a needle head is pressed to the concave portion of the inner mold so as to prevent a material to be injection molded from flowing into a capillary of the needle through the needle rear end.

Effects of the Invention

According to the invention, the needle can be securely fixed to the syringe barrel while steadily keeping adhesivity or sealability around a fixing portion thereof to a syringe nozzle.

It is also possible to prevent an injected material from permeating into a needle capillary through the needle rear end when the syringe barrel is injection molded and to decrease height of a needle end opposite to a needle head extruded toward an inner hollow portion of the syringe barrel.

Further, it is possible to provide a needle-equipped syringe comprising said needle-equipped syringe barrel as a composing element without arising problems derived from a silicone resin component.

DESCRIPTION OF NUMERALS 1 needle-equipped syringe barrel
4 needle holder
10 mold
11 syringe barrel
12 needle
13 piston
14 plunger rod
40 needle holding hole
43 spring
111 outer cylinder
112 flange
113 nozzle (needle fixing portion)
121 needle head
122 rear end portion opposite to needle head
100 cavity plate
200 runner plate
300 core plate
510 needle fitting rod
520 inner mold The Preferred Embodiments Referring now to the drawings, the invention will be described in detail.

Figure 1A:
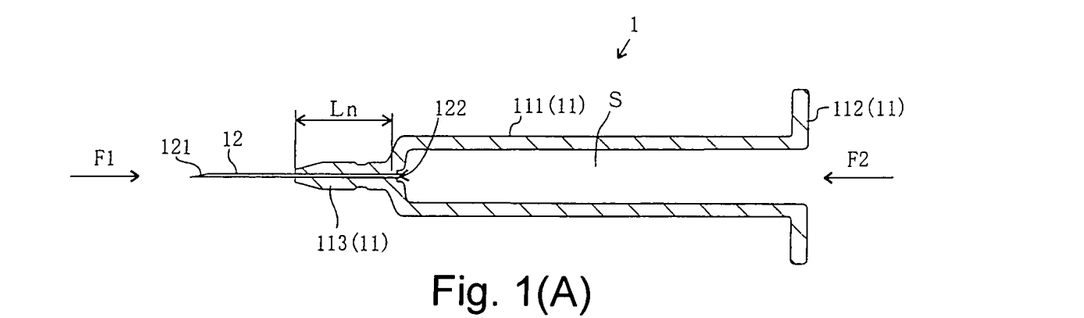
FIG. 1 is an illustration of a needle-equipped syringe barrel of the invention, in which (A) is a side section, (B) is an elevation in the direction F1 and (C) is a rear elevation in the direction F2.
Figure 1B:
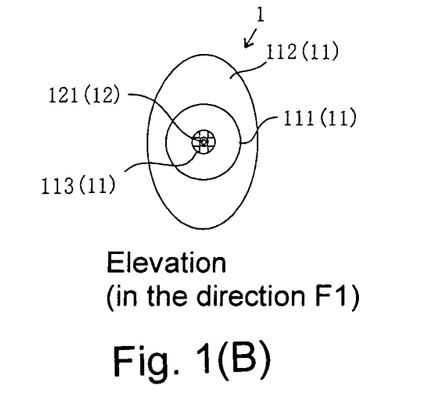
Figure 1C:
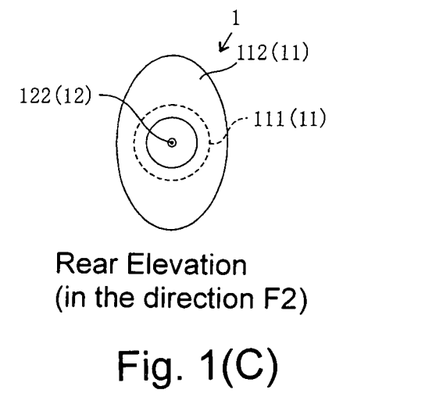

FIG. 1 is an illustration of a needle-equipped syringe barrel of the invention, in which (A) is a side section, (B) is an elevation in the direction F1 and (C) is a rear elevation in the direction F2.

A needle-equipped syringe barrel 1 comprises a synthetic resin syringe barrel 1 and a metal needle 12. The syringe barrel 11 comprises an outer cylinder 111, a flange 112 and a nozzle for fixing the needle 113, while a rear end portion 122 of the needle 12 opposite to a needle head extrudes toward an inner hollow portion S of the syringe barrel 11.

In general, it is considered that force required to root up the needle 12 from the nozzle 113 is different depending on thickness of needles even if structure thereof is the same. The inventor, however, has found a tendency that there exists not much difference in such force when the thickness falls within a certain range. According to the invention, thickness of the needle 12 is 25 to 34 G (about 0.1 to 0.5 mm) based on this finding.

In this invention, it is important that a contact area of the needle 12 and the nozzle 113 is in the range of 11 to 50 mm$^2$. For example, length Ln of the nozzle 113 is about 8.3 to 38 mm when an outer diameter of the needle 12 is 0.42 mm.

In such a dimension, a contact area of 11 mm$^2$ is enough to strongly fix the needle 12 to the syringe barrel 11. In the case of a needle-equipped syringe for general use such as for an intravenous or intramuscular injection, the needle 12 is strongly fixed within the contact area of about 30 mm$^2$ and causes no trouble such as slipping off of the needle 12 from the syringe barrel during injection. Under a condition of higher load to the needle such as an intracartlaginous injection, the contact area is preferably about 50 mm$^2$.

As described above, this invention defines the range of a contact area of the needle 12 and the nozzle 113.

As described above, the needle 12 can be securely fixed to the syringe barrel 11, while steadily keeping adhesivity or sealability around a fixing portion thereof to the syringe nozzle 113. In addition, it is possible to control the contact strength required to root up the needle 12 from the syringe barrel 11 with force of certain strength or more, which makes it easy to classify the needle 12 and the syringe barrel 11 as a metallic material and plastics, respectively.

Figure 2A:
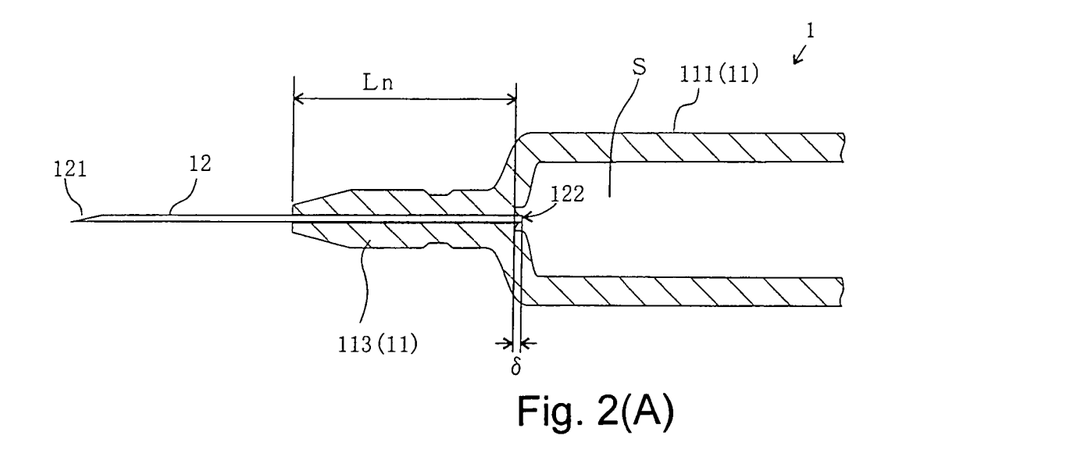
FIGS. 2(A), (B) are enlarged views of a syringe barrel shown in FIG. 1 in the vicinity of a nozzle, in which (B) shows an embodiment in case where length δ extruded toward inner hollow portion S of the syringe barrel is formed larger than that of (A).

FIG. 2(A) is an enlarged view of a syringe barrel 11 shown in FIG. 1(A) to (C) in the vicinity of a rear end portion of the needle 12 opposite to a needle head 121. The rear end portion 122 is pushed against an inner mold during injection molding as will be described later, which makes a concave portion, which is designated by a symbol D in FIGS. 11(A), (B), for the rear end portion 122 formed at the tip of the inner mold shallow, thereby decreasing height δ thereof extruded toward inner hollow portion S of the syringe barrel 11. The height δ means distance from a point of the inner hollow portion S nearest to the nozzle 113 side to the tip of the rear end portion 122 and substantially equals to D (δ=D).

Figure 2B:
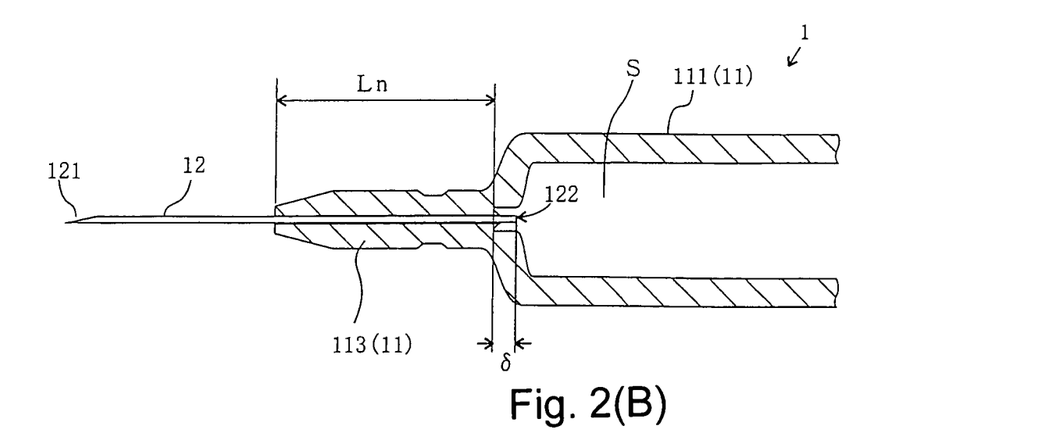

FIG. 2(B) is an enlarged view of a needle-equipped syringe barrel 11 in the vicinity of the rear end portion 122 opposite to the needle head 121, in which a thin cylindrical space is formed to the nozzle 113 side of the inner hollow portion S. As details of the needle-equipped syringe barrel 11 shown in FIG. 1(A) to (C) and FIG. 2 (A) is exactly applicable to what is shown in FIG. 2(B), the syringe barrel of FIG. 2(A) will be detailed in the following.

Although the value δ may vary within the range of 0.4 to 11 mm, the higher the value δ is, the more amount of injection liquid remains in the syringe barrel 11 after injection and the lower the better. When the value δ exceeds 3 mm, a residual amount of the liquid in the syringe barrel 11 might not be negligible from a economic standpoint.

Figures 3A, 3B:
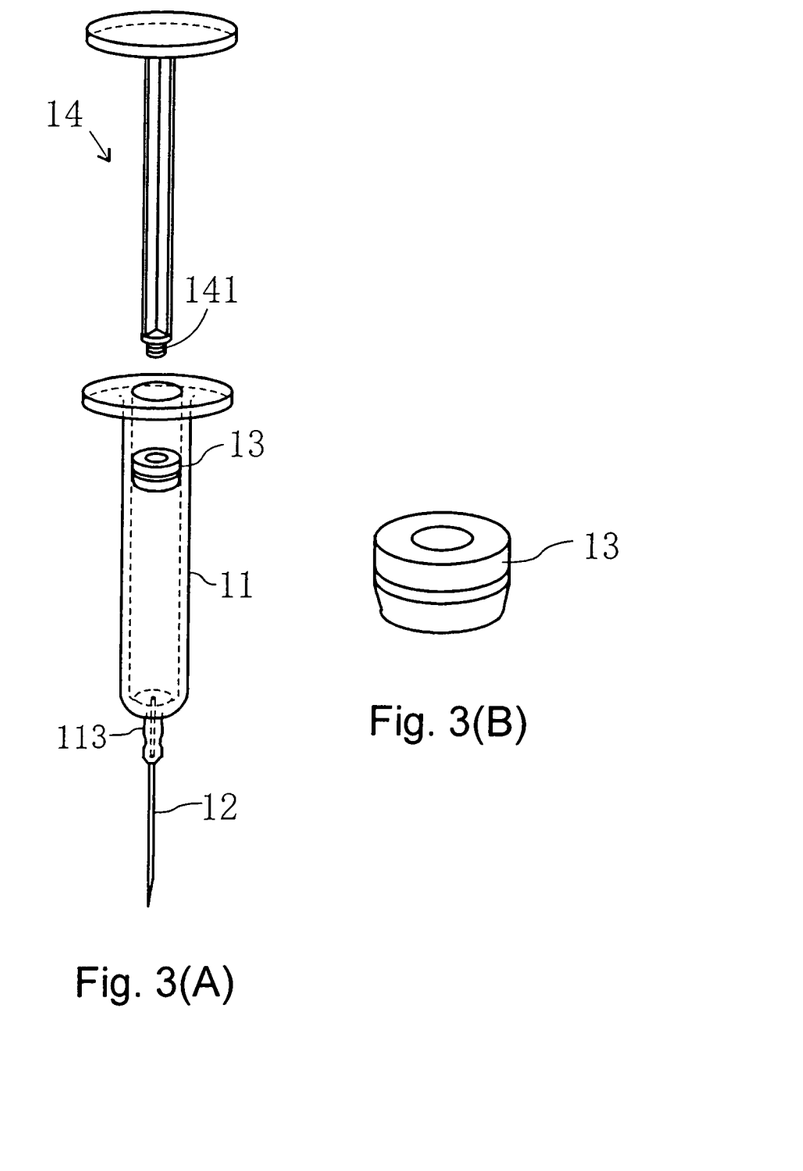
FIG. 3(A) is a schematic illustration of a needle-equipped syringe barrel and a similar syringe which inner surface is not treated and FIG. 3(B) is a schematic illustration of a fluorine resin-treated piston.

When an inner surface of the syringe barrel 11 is treated with a lubricant such as silicone oil, to slide a piston more easily, there may arise various anxiety such as adsorption of effective ingredients in the injection liquid, formation of insoluble substances as a reaction product thereof with the injection liquid, i.e., aggregation, and bad influence upon human body caused by a mixture thereof with the liquid injected in the body. A needle-equipped syringe as shown in FIG. 3 is preferably used when such an inner surface treatment is done. No inner surface treatment, for example, by means of silicone oil is applied to the syringe barrel which is not shown in FIG. 3. A laminating treatment using a fluorine polymer such as PTFE and ETFE is applied to a piston 13 to improve its sliding properties. A screw portion 141 is formed on the end of a plunger rod 14 to fit the piston 13.

Figure 4A:
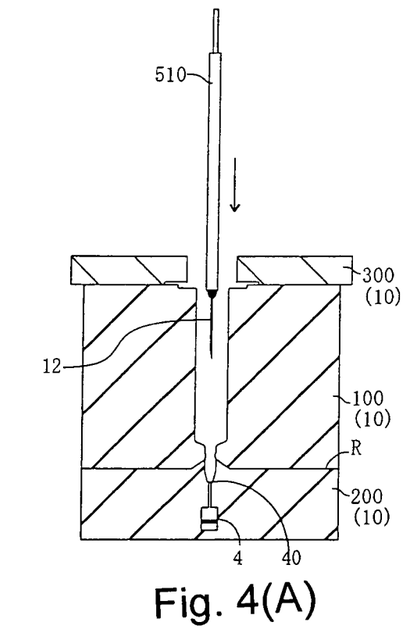
FIG. 4 is a sectional illustration of a mold used for molding a needle-equipped syringe, in which (A) to (D) illustrate a manner to mold the syringe barrel.
Figure 4B:
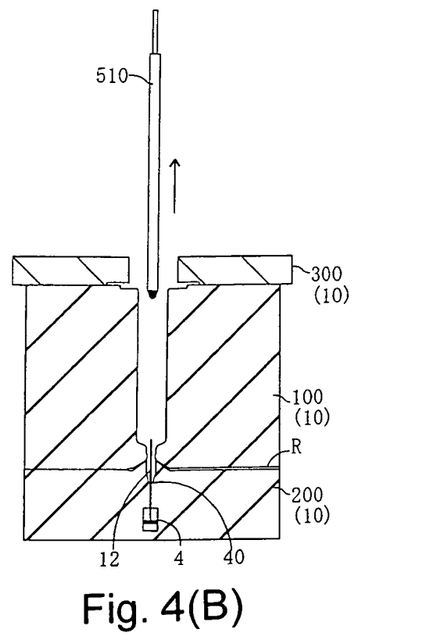
Figure 4C:
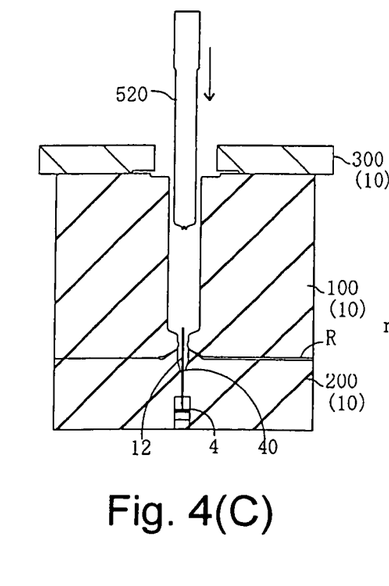
Figure 4D:
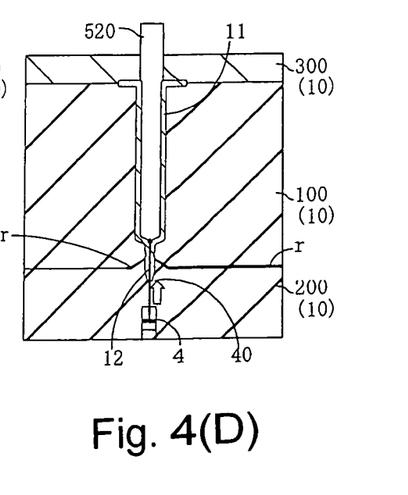
Figure 5:
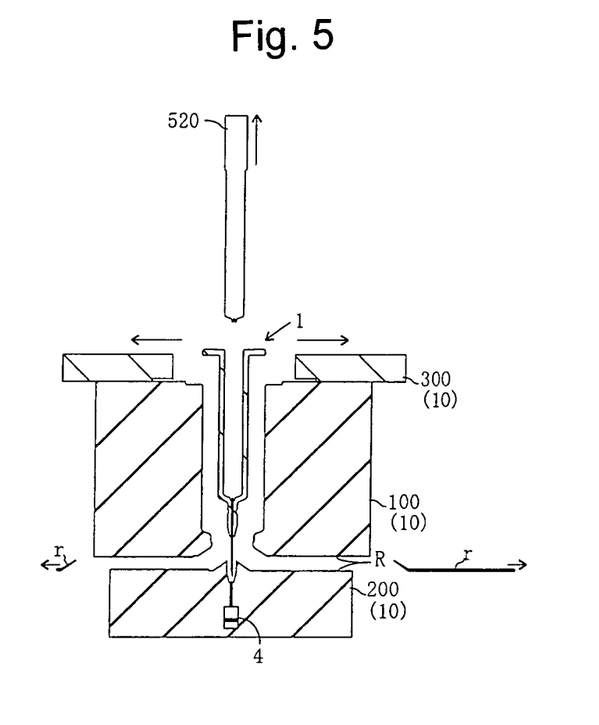
FIG. 5 is a sectional illustration of a mold used for molding a needle-equipped syringe which illustrates a manner to take out the molded syringe barrel.

FIGS. 4 and 5 are sectional illustrations of a mold used for molding a needle-equipped syringe barrel 1 shown in FIG. 1(A) to (C) and FIG. 2(A). FIG. 4 (A) to (D) and FIG. 5 illustrate manners to mold the needle-equipped syringe barrel 1 and to take out the molded product, respectively. In FIGS. 4 and 5, an outer mold of a mold 10 comprises a cavity plate 100, a runner plate 200 and a core plate 300. Other mold composing elements such as guide pins, ejector pins and many other plates are not essential to understand the embodiments of the invention and are omitted herein. A runner R is formed on the boundary surface between the cavity plate 100 and the runner plate 200.

First of all, the core plate 300 is opened as shown in FIG. 4(C) followed by inserting a needle fitting rod 510 provided with the needle 12 on the end into a space formed by the cavity plate 100. Then, the needle is set in a needle holding hole, the rod 510 is receded upward as shown in FIG. 4(B).

An inner mold 520 is inserted into the space formed by the cavity plate 100 after the core plate 300 is opened as shown in FIG. 4(C). A cavity of a definite gap is formed between an outer surface of the inner mold 520 and a hollow wall surface of the cavity plate 100, which is not shown in the figure.

Figure 6A:
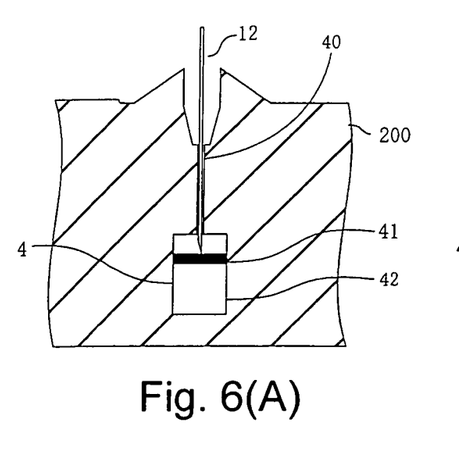
FIG. 6 is a sectional illustration of a needle holder, in which (A) shows a needle head set in a free situation and (B) shows a needle forcibly pushed up to an inner mold side by means of an elastic material.
Figure 6B:
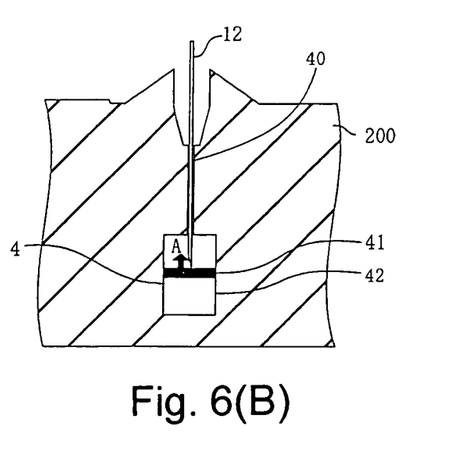

The needle 12 is set in the needle holding hole and the needle head is in a free situation before insertion of the inner mold 520 as shown in FIG. 6(A). After insertion thereof, the needle 12 is forced to push up to the inner mold side by means of an elastic material 42 through a needle head protecting material 41 as shown in FIG. 6(B), the direction of pushing up force added to the needle 12 being designated by a bold black arrow A. The needle head protecting material 41 may be made of soft or elastic material which does not damage the head and is not stuck thereby.

In this situation, the core plate 300 is closed as shown in FIG. 4(D), and a resin is injected into the cavity formed between the outer surface of the inner mold 520 and the hollow wall surface of the cavity plate 100. A runner molded part as a product molded by the runner R being designated by a symbol r.

The cavity plate 100 and the core plate 300 are then opened to take out the molded needle-equipped syringe barrel 1 from the mold 10 as shown in FIG. 5, the runner product r being removed therefrom at the same time.

Figure 7A:
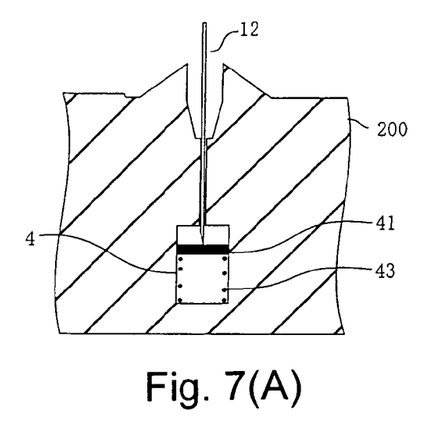
FIG. 7 is a sectional illustration of another needle holder, in which (A) shows a needle head set in a free situation and (B) shows a needle forcibly pushed up to an inner mold side by means of a spring.
Figure 7B:
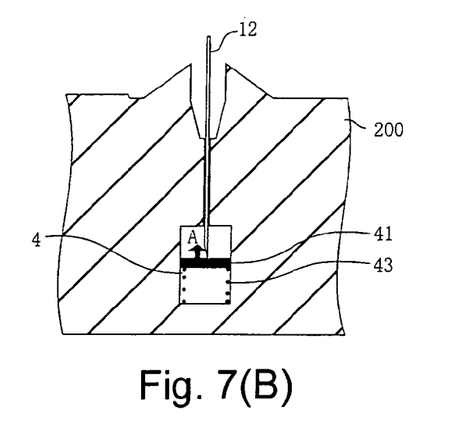

FIGS. 7(A) and (B) is sectional view of another needle holder 4. A spring 43 is arranged in the holder 4 to forcibly push up to the inner mold side which is not shown herein (see, FIGS. 4(C) and (D) and FIG. 5) by means a needle head protecting material 41.

Temperatures of the resin to be molded and the mold may be about 180 to 450° C. and about 30 to 200° C., respectively.

In the case of a multiple mold, the runner may be branched to form runner gates for each cavity.

The resin to be injection molded according to the invention is not limited to specific one, however, preferably includes materials optically transparent materials having glass transition temperature or melting point of 110° C. or higher, for example, polyolefin such as polypropylene, polymethylpentene and cyclic polyolefin, as well as polyethylene terephthalate, polyethylene naphtalate, amorphous polyarylate and the like from a standpoint of properties and strength as the syringe. Cyclic polyolefin is particularly desirable because of its high transparency, steam sterilizability and non-adsorbability to medicine.

A stainless needle-equipped syringe barrel 1 of 42 mm in length was prepared by molding a cyclic polyolefin resin COP in a mold for 1 ml-syringe controlling the resin temperature at 280° C. under a injection pressure of 120 MPa at injection rate of 10 mm/sec (numbers and symbols used herein are similar to those used in FIG. 1(A) to (C)). A contact area between the needle 12 and the nozzle 113, length of the nozzle 113 and extrusion height δ were 17.2 mm$^2$, 13 mm and 1 mm, respectively.

No permeation of the resin was found at the rear end portion 122 opposite to the head of the needle 12 of the molded product.

As a result of root-up test, the needle 12 was pulled out from the outer sylinder under a forcing condition of about 35 N.

What is claimed is:

1. A needle-equipped syringe barrel, comprising:
   an outer cylinder made of synthetic resin, and having an inner hollow portion and a cylindrical space at one side thereof communicating with the inner hollow portion;
   a syringe nozzle extending outwardly from the one side of the outer cylinder and integrally formed with the outer cylinder as one unit;
   a metal needle disposed in the syringe nozzle and having a needle rear end portion protruding into the cylindrical space of the syringe barrel, and a needle tip present on an opposite side of the needle rear end portion, the metal needle having 25 to 34 G in thickness integrally equipped to the syringe nozzle by integral molding; and
   a convex portion extending to an end of the needle rear end portion at a bottom of the cylindrical space and surrounding an outer surface of the needle rear end portion,
   wherein an area where the needle contacts with the syringe nozzle falls in a range of 11 to 50 mm$^2$, and
   the needle rear end portion has a height in a range of 0.4 to 3 mm and located only in the cylindrical space.

2. A needle-equipped syringe, comprising:
   the syringe barrel as claimed in claim 1,
   wherein the syringe barrel is not inner-treated and a piston thereof is laminated with a fluorine resin.

3. The needle-equipped syringe barrel according to claim 1, wherein the needle tip extends to an outside of the syringe nozzle, and
   the needle rear end portion extends into the cylindrical space without extending to the inner hollow portion.

4. The needle-equipped syringe barrel according to claim 3, wherein the cylindrical space has a cross section less than that of the inner hollow portion.

5. The needle-equipped syringe barrel according to claim 1, wherein the convex portion covers substantially an entire outer surface of the needle rear end portion.

6. The needle-equipped syringe barrel according to claim 1, wherein an inner surface of the convex portion contacts with the outer surface of the needle rear end portion.

7. The needle-equipped syringe barrel according to claim 1, wherein the convex portion has a height which is substantially same as the height of the needle rear end portion.

* * * * *